United States Patent
Yi et al.

(10) Patent No.: US 10,492,959 B2
(45) Date of Patent: Dec. 3, 2019

(54) METHOD FOR INDICATING AND ALARMING ABOUT WET LEVEL OF DIAPER

(71) Applicant: Dongguan Southstar Electronics Limited, Dongguan (CN)

(72) Inventors: Jun Yi, Dongguan (CN); Zhihua He, Dongguan (CN); Fangyi Cai, Dongguan (CN); Minghui Du, Dongguan (CN); Weimin Chen, Dongguan (CN); Zhantu Zheng, Dongguan (CN); Jianchao Xu, Dongguan (CN)

(73) Assignee: DONGGUAN SOUTHSTAR ELECTRONICS LIMITED, Dongguan, Guangdong (CN)

(*) Notice: Subject to any disclaimer, the term of this patent is extended or adjusted under 35 U.S.C. 154(b) by 356 days.

(21) Appl. No.: 15/588,682

(22) Filed: May 7, 2017

(65) Prior Publication Data
US 2018/0318146 A1    Nov. 8, 2018

(51) Int. Cl.
*A61F 13/42* (2006.01)
*A61F 13/496* (2006.01)

(52) U.S. Cl.
CPC ........ *A61F 13/42* (2013.01); *A61F 2013/423* (2013.01)

(58) Field of Classification Search
CPC .. A61F 13/42; A61F 13/496; A61F 2013/423; A61F 2013/425; A61F 2013/424; A61F 2013/428; A61M 2205/15
See application file for complete search history.

(56) References Cited

U.S. PATENT DOCUMENTS

| | | | | |
|---|---|---|---|---|
| 4,653,491 A * | 3/1987 | Okada | ............. | A61F 5/4401 128/886 |
| 4,754,264 A * | 6/1988 | Okada | ............. | A61F 5/48 340/573.5 |
| 5,291,181 A * | 3/1994 | DePonte | ............. | A61F 13/42 128/886 |
| 5,392,032 A * | 2/1995 | Kline | ............. | A61F 13/42 128/886 |
| 5,838,240 A * | 11/1998 | Johnson | ............. | A61F 5/48 340/604 |
| 5,849,000 A * | 12/1998 | Anjur | ............. | A61F 13/15203 604/367 |
| 5,875,892 A * | 3/1999 | Martin | ............. | H01L 21/67253 116/206 |
| 5,903,222 A * | 5/1999 | Kawarizadeh | ............. | G01N 27/223 128/886 |

(Continued)

*Primary Examiner* — Lisa M Caputo
*Assistant Examiner* — Tran M. Tran
(74) *Attorney, Agent, or Firm* — Leong C. Lei

(57) ABSTRACT

A method for indicating and alarming about wet level of a diaper involves using a humidity sensor to perform relative humidity detection on the diaper, when the detected relative humidity is below 50% rh~60% rh, showing the diaper's wet level as 0% rh, and when the detected relative humidity is 85% rh~95% rh or more, showing the diaper's wet level as 100% rh, wherein functional conversion is performed to convert the relative humidity ranging between 60% rh and 85% rh~95% rh proportionally into the diaper's wet level between 0% rh and 100% rh.

3 Claims, 1 Drawing Sheet

(56) References Cited

U.S. PATENT DOCUMENTS

| | | | | |
|---|---|---|---|---|
| 5,908,411 A * | 6/1999 | Matsunari | A61F 13/42 340/604 |
| 6,097,297 A * | 8/2000 | Fard | A61F 13/42 128/886 |
| 6,200,250 B1 * | 3/2001 | Janszen | A61F 13/42 493/334 |
| 6,583,722 B2 * | 6/2003 | Jeutter | A61F 13/42 340/573.1 |
| 6,603,403 B2 * | 8/2003 | Jeutter | G06K 19/0716 340/604 |
| 7,295,125 B2 * | 11/2007 | Gabriel | A61F 13/42 340/604 |
| 7,355,090 B2 * | 4/2008 | Ales, III | A61F 13/42 604/361 |
| 7,498,478 B2 * | 3/2009 | Long | A61F 13/42 604/361 |
| 7,700,821 B2 * | 4/2010 | Ales, III | A61F 13/42 604/361 |
| 7,977,529 B2 * | 7/2011 | Bergman | A61F 13/42 604/361 |
| 8,130,094 B2 * | 3/2012 | Lu | G16H 40/20 340/539.1 |
| 8,172,154 B1 * | 5/2012 | Figley | F24F 11/30 236/44 A |
| 8,274,393 B2 * | 9/2012 | Ales | A61F 13/42 340/604 |
| 8,314,284 B1 * | 11/2012 | Novello | A61F 13/505 604/361 |
| 8,381,575 B2 * | 2/2013 | Seo | G01N 27/223 73/29.02 |
| 8,421,636 B2 * | 4/2013 | Collette | A61F 13/42 340/539.12 |
| 8,697,933 B2 * | 4/2014 | Ales, III | A61F 13/42 604/361 |
| 8,975,465 B2 * | 3/2015 | Hong | A61F 13/42 604/359 |
| 9,119,748 B2 * | 9/2015 | Abraham | A61F 13/42 |
| 9,204,806 B2 * | 12/2015 | Stivoric | G06F 19/3418 |
| 9,224,102 B2 * | 12/2015 | Barda | A61F 13/42 |
| 9,380,977 B2 * | 7/2016 | Abir | A61F 13/42 |
| 9,408,757 B2 * | 8/2016 | Elfstrom | A61F 13/42 |
| 9,585,795 B2 * | 3/2017 | Bosaeus | A61F 13/42 |
| 9,820,891 B2 * | 11/2017 | Abir | A61F 13/42 |
| 9,844,338 B2 * | 12/2017 | Abir | A61F 13/42 |
| 9,895,273 B2 * | 2/2018 | Xu | A61F 13/42 |
| 9,931,251 B2 * | 4/2018 | Euliano | A61F 13/42 |
| 9,937,082 B2 * | 4/2018 | Chen | G08B 25/08 |
| 10,285,871 B2 * | 5/2019 | Arizti | A61F 13/42 |
| 10,292,112 B2 * | 5/2019 | LaVon | A61F 13/42 |
| 10,307,303 B2 * | 6/2019 | Carney | A61F 5/48 |
| 2002/0021220 A1 * | 2/2002 | Dreyer | A47K 11/04 340/573.1 |
| 2004/0236302 A1 * | 11/2004 | Wilhelm | A61F 13/42 604/389 |
| 2005/0156744 A1 * | 7/2005 | Pires | A61F 13/42 340/573.5 |
| 2008/0074274 A1 * | 3/2008 | Hu | A61F 13/42 340/573.5 |
| 2010/0241094 A1 * | 9/2010 | Sherron | A61F 13/42 604/361 |
| 2015/0164703 A1 * | 6/2015 | Bae | A61F 13/42 324/693 |
| 2016/0120455 A1 * | 5/2016 | Pop | A61B 5/208 600/301 |
| 2016/0166438 A1 * | 6/2016 | Rovaniemi | A61F 13/00059 600/301 |
| 2017/0000655 A1 * | 1/2017 | Mashin-Chi | A61F 13/42 |

* cited by examiner

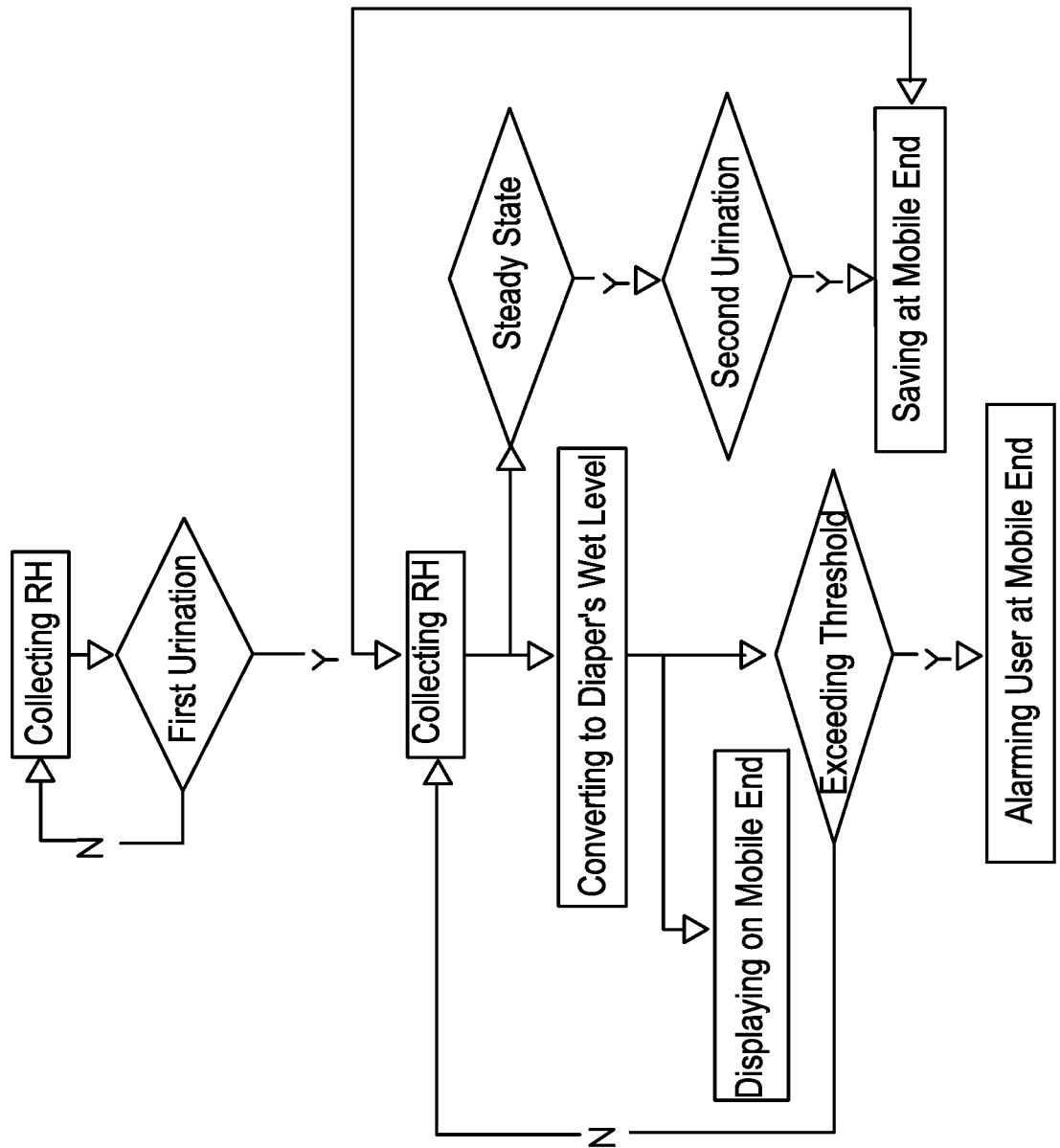

METHOD FOR INDICATING AND ALARMING ABOUT WET LEVEL OF DIAPER

BACKGROUND OF THE INVENTION

1. Technical Field

The present invention relates to nursing of infants, and more particularly to a method for indicating and alarming about wet level of a diapers.

2. Description of Related Art

When having their infants using diaper pants or diapers, parents tend to touch the diaper with hands frequently in order to determine whether the diaper is too wet and needs to be replaced. Disadvantages related to this practice are many. First, manual test is time consuming and not accurate. Secondly, manual test is impossible to be conducted in a continuous manner, and late knowing about wetness can lead to a baby's diaper rash. Thirdly, frequent testing touches may upset the infant.

One method for indicating wetness of diapers available in the market needs parents' frequent check. This method wastes time and may cause babies' skin allergy or inflammation if parents fail to detect wetness timely. Another approach to this involves placing a test probe on a diaper's stay-dry layer (the inner surface of a diaper). However, the test probe contacting human skin directly may make infants uncomfortable and needs frequent cleaning. Still another existing scheme uses a humidity sensor to detect a diaper's relative humidity. Nevertheless, most parents are awkward with intuitively recognizing diapers' wet level from relative humidity. Once the diaper is overused without timely alarm, the infant may develop a diaper rash.

SUMMARY OF THE INVENTION

In view of this, the objective of the present invention is to address the shortcomings of the prior art by providing a method for indicating and alarming about wet level of a diaper, wherein relative humidity not familiar to general users is converted into understandable wet level of diapers, making the use of diapers more convenient to users.

For achieving the foregoing objective, the present invention adopts the following technical scheme:

A method for indicating and alarming about wet level of a diaper uses a humidity sensor to test the relative humidity in the diaper. When it is detected that the relative humidity is below 50% rh~60% rh, the diaper's wet level is shown as 0% rh. When the detected relative humidity is 85% rh~95% rh or more, the diaper's wet level is shown as 100% rh. Functional conversion is performed to convert the relative humidity ranging between 60% rh and 85% rh~95% rh proportionally into the diaper's wet level between 0% rh and 100% rh. When a first urination is detected, the detected relative humidity is converted into the diaper's wet level and displayed through a mobile end. A threshold for triggering an alarm that asks for diaper change is set by a user. When the diaper's wet level reaches or exceeds this threshold, the mobile end alarms the user for diaper change.

As a preferred scheme, the method for detecting the first urination comprises:

(1) determining that Condition 1 is satisfied if relative humidity detected by the humidity sensor lastly is greater than relative humidity of previous N times and is 1% rh~3% rh greater than a minimum among the relative humidity of the previous N times;

(2) determining that Condition 2 is satisfied and the first urination has happened if relative humidity detected in continuous M times satisfies Condition 1, and the relative humidity detected in the Mth time is 3% rh~6% rh greater than a minimum among the relative humidity of the previous N+M times; and (3) starting to detect a second urination when variation of the relative humidity becomes steady.

As a preferred scheme, the N and M are both 7.

As a preferred scheme, the mobile end is a smartphone, a smartwatch or a tablet computer.

The present invention has significant advantages and beneficial effects over the prior art. Particularly, it is learned from the foregoing technical scheme that:

the disclosed indication method converts relative humidity that are unfamiliar to users into understandable wet level of diapers, so that users can easily know diaper's wet level, and the mobile end set with the threshold can trigger alarm for diaper change, so as to protect infants from a diaper rash and to save costs for diapers, making use of diapers more convenient.

The invention as well as a preferred mode of use, further objectives and advantages thereof will be best understood by reference to the following detailed description of illustrative embodiments when read in conjunction with the accompanying drawings.

BRIEF DESCRIPTION OF THE DRAWINGS

FIG. 1 is a flowchart of a preferred embodiment of the present invention.

DETAILED DESCRIPTION OF THE INVENTION

The present invention discloses a method for indicating and alarming about wet level of a diaper. It involves uses a humidity sensor to perform relative humidity detection on the diaper. When the detected relative humidity is below 50% rh~60% rh, the diaper's wet level is shown as 0% rh. When the detected relative humidity is 85% rh~95% rh or more, the diaper's wet level is shown as 100% rh. Functional conversion is performed to convert the relative humidity ranging between 60% rh and 85% rh~95% rh proportionally into the diaper's wet level between 0% rh and 100% rh. The disclosed method for indicating a diaper's wet level first detects a first urination. If the infant has not urinated, the diaper's wet level is shown as 0% rh. Where urination is confirmed, if the relative humidity is below 60% rh, it is determined that the diaper's wet level is low and to be shown as a low value (1% rh~10% rh).

When the first urination is detected, the detected humidity is converted into the diaper's wet level and displayed through a mobile end. The user sets a threshold where an alarm for diaper change is triggered. When diaper's wet level reaches or exceeds this threshold, the mobile end alarms the user for diaper change. The mobile end is a smartphone, a smartwatch or a tablet computer. This alarm method is beneficial because parents can set and change the threshold according to the infant's current skin conditions. When the infant's skin is too weak to tolerate high wet level, the threshold can be lowered.

In the present embodiment, the method for detecting the first urination has the following steps:

As Step (1), the method determines that Condition 1 is satisfied if relative humidity detected by the humidity sensor lastly is greater than relative humidity of previous N times and is 1% rh~3% rh greater than a minimum among the relative humidity of the previous N times. in the present embodiment, N is 7, so as shown in FIG. 1, Condition 1 is satisfied when the relative humidity detected by the humidity sensor lastly is greater than relative humidity of previous 7 times and is 1% rh~3% rh greater than a minimum among the relative humidity of the previous 7 times.

As Step (2), the method determines that Condition 2 is satisfied and the first urination has happened if relative humidity detected in continuous M times satisfies Condition 1, and the relative humidity detected in the Mth time is 3% rh~6% rh greater than a minimum among the relative humidity of the previous N+M times; Condition 2 is satisfied and the first urination has happened when the relative humidity detected in continuous 7 times satisfies Condition 1, and the relative humidity detected in the 7th time is 3% rh~6% rh greater than a minimum among the relative humidity of the previous 7 times.

As Step (3), when variation of the relative humidity becomes steady, the method starts to detect a second urination. The term "becomes steady" refers to that the time for relative humidity to increase every 0.1% rh is more than 20 seconds. The interval for detecting relative humidity is 0.5~3 seconds.

The disclosed indication method is designed with the feature of converting relative humidity is unfamiliar to users into understandable wet level of diapers, so that users can easily know diaper's wet level. Besides, the mobile end set with the threshold can trigger alarm for diaper change, so as to protect infants from a diaper rash and to save costs for diapers, making use of diapers more convenient.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A method for indicating and alarming about wet level of a diaper, comprising the following steps: using a humidity sensor to perform relative humidity detection on the diaper; wherein the diaper's wet level is shown as 0% rh when detected relative humidity is below 50% rh~60% rh, and the diaper's wet level is shown as 100% rh when detected relative humidity is 85% rh~95% rh or more; wherein functional conversion is performed to convert the relative humidity ranging between 60% rh and 85% rh~95% rh proportionally into the diaper's wet level between 0% rh and 100% rh; converting the detected relative humidity into the diaper's wet level when a first urination is detected and displaying the level through a mobile end, and using the mobile end to alarm a user about diaper change when the diaper's wet level reaches or exceeds a threshold set by the user for trigger an alarm about diaper change; wherein detection of the first urination comprises the following steps:

(1) determining that Condition 1 is satisfied when a relative humidity collected by the humidity sensor lastly is greater than relative humidity of previous N times and is 1% rh~3% rh greater than a minimum among the relative humidity of the previous N times;
   (2) determining that Condition 2 is satisfied and the first urination has happened when relative humidity detected in continuous M times satisfies Condition 1, and the relative humidity detected in the Mth time is 3% rh~6% rh greater than a minimum among the relative humidity of the previous N+M times; and
   (3) starting to detect a second urination when variation of the relative humidity becomes steady.

2. The method of claim 1, wherein values of N and M are both 7.

3. The method of claim 1, wherein the mobile end is a smartphone, a smartwatch or a tablet computer.

* * * * *